US006875861B1

(12) United States Patent
Besemer et al.

(10) Patent No.: US 6,875,861 B1
(45) Date of Patent: *Apr. 5, 2005

(54) PROCESS FOR PRODUCING NITROSONIUM IONS

(75) Inventors: Arie Cornelis Besemer, Amerongen (NL); Jan Matthijs Jetten, Zeist (NL); Thomas Jaschinski, Mannheim (DE); Ronald Tako Marinus Van Den Dool, Culemborg (NL)

(73) Assignee: SCA Hygiene Products Zeist B.V., Zeist (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/913,603
(22) PCT Filed: Feb. 24, 2000
(86) PCT No.: PCT/NL00/00118

§ 371 (c)(1),
(2), (4) Date: Dec. 20, 2001

(87) PCT Pub. No.: WO00/50388

PCT Pub. Date: Aug. 31, 2000

(30) Foreign Application Priority Data

Feb. 24, 1999 (EP) .......................................... 992005363

(51) Int. Cl.[7] .......................... C07H 15/00; C07H 1/00; C07G 17/00
(52) U.S. Cl. ................... 536/123.1; 536/18.5; 536/105; 536/124
(58) Field of Search ............................... 536/105, 18.5, 536/123.1, 124

(56) References Cited

U.S. PATENT DOCUMENTS 3,632,802 A * 1/1972 BeMiller et al.
4,983,748 A   1/1991 Tsai et al.
5,747,658 A   5/1998 Veelaert et al.

FOREIGN PATENT DOCUMENTS

DE    3705785      9/1988
EP    124439      11/1984
WO    95/07303     3/1995
WO    99/23117     5/1999

OTHER PUBLICATIONS

A.E.J. De Nooy et al., "On the Use of Stable Organic Nitroxyl Radicals for the Oxidation of Primary and Secondary Alcohols", *Synthesis*, pp. 1153–1174.
Nelly Blumenkrantz et al., "New Method for Quantitative Determination of Uronic Acids", *Anal. Biochem*, 54 (1973) 484.
Bobbitt, J.M. et al., "Organic Nitrosinium Salts as Oxidants in Organic Chemistry", Heterocycles, XX,XX, vol. 27, No. 2, Jan. 1, 1988, pp. 509–533.
"Römp Lexikon, 10. Auflage", 1999, George Thieme Verlag, Stuttgart.
De Nooy, A.E.J., et al., "Highly Selective Tempo Medicated Oxidation of Primary Alcohol Groups in Polysaccharides", Recueil des Travaux Chimiques des Pays–Bas, NL, Elsevier Science Publishers, Amsterdam, vol. 113, No. 3, pp. 165–166 Mar. 1, 1994.
Luner, P., et al., "The Effect of Chemical Modification on The Mechanical Properties of Paper, 1. Oxidation and Reduction of Rayon Fibers", *Tappi*, 50(1): 37–39, 1967.
Young, R. A., "Bonding of Oxidized Cellulose Fibers and Interaction with Wet Strength Agents", *Wood & Fiber*, [The Society of Wood Science & Technology] 10(2): 112–119, 1978.
Chang, P.S. and Robyt, J.F., "Oxidation of Primary Alcohol Groups of Naturally Occurring Polysaccharides with 2,2,6, 6–Tetramethyl–1–Piperidine Oxoammonium Ion", *J. Carbohydrate Chemistry*, 15(7): 819–830, 1996.
Chemical Abstracts, XP002110902 & JP 50 054684, 82: 20, Nov. 17, 1975.
Chemical Abstracts, Columbus, Ohio, US; abstract No. 122628, XP002136587 abstract & SU 592 905, 89: 14, Oct. 2, 1978.
Fieser, L. F. & Fieser, M., "Acetals and Ketals", *Organic Chemistry*, (Reinhold Pub. Corp. New York) 215, 1956.
Horton, D., et al., "Preparation of Unsubstituted 6–Aldehydocelluloses by Photolysis of 6–Azido–6–Deoxycelluloses", *Carbohydrate Research*, IElsvier Scientific Publ, Amsterdam, Belgium) 26: 1–19, 1973.
Nevell, T. P. and Zeronian, S. H., *Cellulose Chemistry and its Applications*, 1985, Ellis Horwood Ltd., Chichester, Great Britain, XP002136586, 256, 1985.
Roberts & Caserio, "Reactions at the Carbonyl Group, Chapter 14", *Organic Chemistry*, (W.A. Benjamin, Inc.) 442–452, 1965.
Semmelhack, M. F., et al., "Oxidation of Alcohols to Aldehydes with Oxygen and Cupric Ion, Mediated by Nitrosonium Ion", *J. Am. Chem. Soc.*, 106: 3374–3376, 1984.

* cited by examiner

Primary Examiner—James O. Wilson
Assistant Examiner—Traviss C. McIntosh, III
(74) Attorney, Agent, or Firm—Burns, Doane, Swecker & Mathis LLP

(57) ABSTRACT

A process for producing nitrosonium ions is described, in which a nitroxyl compound such as TEMPO is oxidized using an oxidizing agent in the presence of a complex of a transition metal such as Mn, Fe, Cu, and a complexing agent such as a polyamine. The process is useful for the oxidation of carbohydrates containing at least 1 cyclic monosaccharide chain group carrying a carbaldehyde group per 100 or per 25 monosaccharide units and per molecule.

14 Claims, No Drawings

PROCESS FOR PRODUCING NITROSONIUM IONS

The invention relates to the production of nitrosonium ions (oxoammonium ions) by oxidation of nitroxyl radicals, especially 2,2,6,6-tetramethylpiperidin-1-oxyl (TEMPO). The nitrosonium ions can be used as a catalytic oxidising agent for the selective oxidation of primary alcohols to aldehydes.

Such a process in which TEMPO is reoxidised by chemical means is known from a review by De Nooy in *Synthesis* 1996, 1153–1174 and from WO 95/07303.

It was found according to the invention that oxidation of alcohol functions, especially primary alcohol functions, using nitrosonium ions, can be carried out without using chlorine-based oxidising agents and with the use of hydrogen peroxide or oxygen as the ultimate oxidising agent. The oxidation according to the invention is performed using transition complexes of a transition metal and a complexing agent as intermediate oxidants. This oxidation, when carried out on primary alcohols, results in the formation of aldehydes. The aldehydes may be present in the (hemi)acetal form and related structures. The process is particularly suitable for oxidising carbohydrates having primary alcohol functions. An adaptation of the oxidation of the invention can be used to oxidise secondary alcohols, especially carbohydrates, to keto derivatives. The process of the invention is further defined by the characterising features of the appending claims.

In the following description, reference is made to TEMPO only for the sake of simplicity, but it should be understood that other suitable nitroxyls, i.e. organic nitroxyl compounds lacking $\alpha$-hydrogen atoms, such as 2,2,5,5-tetramethylpyrrolidine-N-oxyl (PROXYL), 4-hydroxy-TEMPO, 4-acetamido-TEMPO and derivatives thereof and those described in WO 95/07303 can be substituted for TEMPO. These di-tert-alkyl nitroxyls are especially suitable for selectively oxidising primary alcohols to aldehyde functions, in particular in the presence of secondary alcohol functions that should not be oxidised. Less sterically hindered nitroxyls, such as 4,4-dimethyloxazolidine-N-oxyl (DOXYL), are suitable for preferentially oxidising secondary alcohols to keto functions, for example in the production of keto starch. The active oxidising species is the nitrosonium ion (oxoammonium ion $>N^+=O$), that is produced in situ by oxidation of the corresponding hydroxylamine and nitroxyl radical. If desired, the reaction can be performed in two steps, the production of the nitrosonium ion being the first and the oxidation of the alcohol function being the second.

A catalytic amount of nitroxyl is preferably 0.1–25% by weight, based on the primary alcohol, or 0.1–25 mol % with respect to the primary alcohol. The nitroxyl may also be immobilised, e.g. by coupling of the hydroxyl group of 4-hydroxy-TEMPO to a suitable carrier, or in the form of a polymeric nitroxyl such as:
—[(CH$_3$)$_2$C—NO.—C(CH$_3$)$_2$—A—]$_n$—, wherein A may be an alkylene group and/or a heteroatom, and n is a number form e.g. 10 up to several hundreds.

The process of the invention results in oxidation of primary alcohols initially to the corresponding aldehydes. If required the primary products can be further oxidised to the corresponding carboxylic acids by using known oxidising agents such as hypochlorite, chlorite, hydrogen peroxide or by using TEMPO-mediated oxidation under more vigorous conditions such as an increased temperature e.g. from 40–80° C., or for prolonged exposure to the reaction conditions. Alternatively, the aldehyde/carboxylic acid ratio can be increased by using relative low pH's (e.g. pH 3–7), by controlled addition of oxidising agent, by lowering the oxygen concentration, or by first preparing the nitrosonium ion solution (two-step process).

The present process is especially favourable for the selective oxidation of primary hydroxyl groups in alcohols having a secondary alcohol function in addition to the primary alcohol, such as 1,6-octanediol, 1,9-octadecanediol, steroid hormones, sugar alcohols, glycosides (flavour precursors), and in particular carbohydrates having primary alcohol functions. The carbohydrates may be monosaccharides, such as glucose, fructose, disaccharides, such as sucrose, maltose, lactose, oligosaccharides and polysaccharides. The oligo- and polysaccharides may be of any type, e.g. glucans such as starch, starch components (i.e. amylose, amylopectin, dextrins), pullulan ($\alpha$-1,4-$\alpha$-1,4-$\alpha$-1,6-glucan), chitin, lichenin etc., furanofructans such as inulin and levan, galactans, arabinogalactans, furanoid pentosans (xylans), (galacto) mannans (guar, locust bean gum), bacterial exopolysaccharides (EPS) and the like and derivatives of such carbohydrates, such as hydrolysates. These oligo- and polysaccharides include heterosaccharides, i.e. those which have different structural units, even if those different units themselves may not have primary hydroxyl groups such as uronic acid units, e.g. in xanthan and carbohydrates derived form algae. The carbohydrates to be oxidised according to the invention include glycosides and other protected carbohydrates. Further examples are glyconic acids, such as lactobionic acid delta-lactone, that can be oxidised to glycaric acids and the like.

A distinct group of compounds suitable for oxidation with the present process consists of hydroxyalkylated carbohydrates such as hydroxypropyl starch or hydroxyethyl inulin, which result in an alternative way for producing formylalkyl carbohydrates. Other suitable carbohydrate substrates in which at least a part of the (6-) hydroxymethyl groups are intact, include for example (2- and 3-) carboxymethyl carbohydrates.

The oxidation of carbohydrates containing primary hydroxyl groups results in the corresponding carbohydrates containing aldehydes and, if desired, to carboxylic acids, with intact ring systems. Examples include $\alpha$-1,4-glucan-6-aldehydes, $\beta$-1,4-glucan-6-aldehydes, $\beta$-2,1-fructan-6-aldehydes and $\beta$-2,6-fructan-1-aldehydes. These products are useful intermediates for functional carbohydrates wherein the aldehyde groups are further reacted with e.g. amine compounds and the like. They are also useful intermediates for crosslinked carbohydrates, in which the aldehyde groups are further reacted with e.g. diamine reagents.

The catalysts to be used according to the invention are complexes of transition metals, i.e. coordination compounds between a transition metal and an organic molecule as a complexing agent having one or more free electron pairs, especially nitrogen compounds. Suitable nitrogen compounds include amino acids, phenanthrolines and other polyamines. A polyamine, which forms a complex with the transition metal, is understood to refer to compounds which comprise at least two amine nitrogen atoms, separated by at least two carbon atoms. Preferably, the polyamines comprise at least three nitrogen atoms which in each case are separated by two or more, in particular two or three, more in particular two, carbon atoms. The remaining valencies of the nitrogen atoms are preferably bound with small alkyl groups, in particular methyl. It is also possible for the polyamines to have ether or alcohol functions. The polyamines can be linear or cyclic. The polyamines should be alkaline, i.e. should not contain acid functions. Examples of polyamines which can be employed are 2,2'-bipyridyl, 2,2'-bipyrrole, 2-(dimethylaminomethyl)pyridine, tetramethylethylenediamine, pentamethyldiethylenetriamine, 1,4-dimethylpiperazine, 1,4,7-trimethyl-1,4,7-triazonane (=triazacyclononane), 1,4, 7-trimethyl-1,4,7-triazecane, 1,4,7,10-tetramethyl-1,4,7,10-tetraazacyclododecane, 1,2-bis(4-methyl-1-piperazinyl)-ethane, 1,2-bis(4,7-dimethyl-1,4,7-triazonan-1-yl)ethane, and the corresponding compounds wherein one or more of the said methyl groups have been replaced by, for example, ethyl groups. It is also possible to use porphin and other porphyrins and corresponding macrocyclic polyamine compounds. Histidine and comparable amino acids having an additional nitrogen atom, and their oligopeptides such as histidyl-histidine, are other examples of suitable complexing agents. Preference is given to compounds of the bipyridyl type, triazonane type and to amines whose remaining valencies are linked to methyl groups. The counterions required for neutrality of the complexes may be common, preferably non-toxic counterions such as oxide, halide, perchlorate, acetylacetonate, nitrate, sulphate and the like.

Transition metals to be used in the metal complexes include especially those of the fourth period of the periodic table of elements from vanadium to zinc, preferably manganese, iron, cobalt, nickel and copper, in particular manganese, iron, cobalt and copper. The corresponding metals from the higher periods may also be used, such as in particular ruthenium. The metal complexes require hydrogen peroxide, alkyl and ar(alk)yl hydroperoxides (such as tert-butyl hydroperoxide), oxygen or chlorite as an ultimate electron acceptor. About one metal atom to two to four nitrogen atoms of the complexing agent can suitably be used.

The metal complex may be used in a catalytic amount, e.g. in about an equimolar amount with respect to the nitroxyl compound. Suitable amounts of metal complexes are for example 1–25 mol % with respect to the alcohol to be oxidised.

The process of the invention can be performed under relatively mild conditions, e.g. at a pH between 5 and 10, and at a temperature between 15 and 60° C. (both depending on the particular metal complex). The reaction medium can be an aqueous medium, or a homogeneous mixed medium, e.g. of a mixture of water and a secondary or tertiary alcohol or an ether/water mixture, or a heterogeneous medium, e.g. a mixture of water and a water-immiscible organic solvent such as a hydrophobic ether, a hydrocarbon or a halogenated hydrocarbon. In the latter case, the metal complex and/or the nitroxyl and the oxidising agent may be present in the aqueous phase and the alcohol substrate and the aldehyde or ketone product may be present in the organic phase. If necessary, a phase transfer catalyst may be used. The reaction medium can also be a solid/liquid mixture, in particular when the nitroxyl is immobilised on a solid carrier. A heterogeneous reaction medium may be advantageous when the substrate or the product is relatively sensitive or when separation of the product from the other reagents may present difficulties.

The invention also pertains to novel carbohydrate oxidation products and derivatives thereof, which can be obtained with the process of the invention. These include polysaccharides in which at least 1 hydroxymethyl per 100, especially per 50 or even per 25, monosaccharide units has been converted to a carbaldehyde group, whether or not in hermiacetal or similar form, with the proviso that on average each molecule contains at least 1 carbaldehyde group other than a possible (hemiacetalised) aldehyde group at the reducing end of an oligo- or polysaccharide. When the carbohydrate is starch, the degree of oxidation is at least one carbaldehyde group per 25 anhydroglucose units. The carbaldehyde group is preferably present in chain (backbone) units, rather than in branch or terminal units. The novel products include glycoside derivatives, i.e. products which, in addition to an acetalised end group have at least one carbaldehyde group obtainable by oxidation of non-galactose hydroxymethylene groups. In the products of the invention, the monosaccharide rings that carry the carbaldehyde group are largely intact. The only common carbohydrate derivatives having a predominant content of aldehyde groups are periodate-type oxidation products of starch, cellulose and the like, in which the rings bearing the aldehyde groups are broken. The aldehyde carbohydrates covered by the present invention are especially of types other than the cellulose or pentosan type (or derivatives such as carboxymethylated, alkylated, hydroxyalkylated cellulose). The products obtainable according to the invention may contain, in addition to the aldehyde groups, other functional groups, especially carboxyl groups obtained by further oxidation or by carboxyalkylation.

The novel derivatives of the invention are very suitable as thickeners, viscosifiers, stabilisers, wet strength additives, water-absorbing polymers and the like, and especially as starting materials for further functionalisation, especially with alcohols, amines, and other agents capable of coupling with an aldehyde function. Such agents include crosslinking agents (diamines, diols and the like), which can be used to crosslink the carbohydrates or to couple them to amino acids, proteins, active groups etc.

The process of the invention can also advantageously be used for modifying biopolymers such as starch, non-wood cellulose to allow derivatisation or to adapt viscosity and other physical or chemical properties such as (textile) strength, dyeability, etc.

The invention also pertains to derivatives obtained by coupling of the aldehyde carbohydrates described above with e.g. amines, especially by reductive amination, to produce imino or amino derivatives of carbohydrates as defined in the appending claims. Also, the aldehyde carbohydrates can be reacted acetalised with hydroxy-functionalised compounds, e.g. glycolic acid, for further derivatisation.

EXAMPLES

General

Uronic acid (6-COOH of hexopyranose units) contents were determined using the Blumenkrantz et al. method (*Anal. Biochem.* (1973) 54, 484), using boric acid (0.0125 M) in concentrated sulphuric acid, adding 3-hydroxybiphenyl and measuring the extinction at 520 mm.

Aldehyde contents were determined either by a subtractive method (determining the uronic acid content before and after of oxidation of aldehydes with chlorite and hydrogen peroxide), or by addition of hydroxylamine hydrochloride to produce an oxime and back-titration of liberated hydrochloric acid, or by $^{13}C$ NMR spectroscopy (intensity of C6 signal of aldehyde with respect to C1 of anhydroglucose unit, or intensity of C6 (C=N) in the oxime).

Example 1

C6 Oxidation of Methylglucopyranoside with TEMPO/Mn/Hydrogen Peroxide

Sixty mg of α-methylglucopyranoside, 30 mg of Mn complex with 1,4,7-trimethyl-1,4,7-triazonane and 500 mg TEMPO (lower amounts work equally well) were dissolved in 100 ml of demineralised water. The reaction temperature was raised to 55–60° C. and the pH was maintained at 8.5. Diluted hydrogen peroxide (31 μl 30% in 10 ml demineralised water) was added over 5 h. After overnight reaction, the C6 carboxyl and C6 aldehyde contents were qualitatively shown using DIONEX HPAEC. A sample was reduced with sodium borohydride at pH 8 to confirm the presence of aldehyde functions. The carboxyl content was determined using the Blumenkrantz method to be 20%. After further oxidation of aldehyde (hemiacetal) with sodium chlorite and hydrogen peroxide, the carboxyl content was 26%. Thus the aldehyde content was 6%.

Example 2

Oxidation of Methylglucopyranoside with TEMPO/Mn/Hydrogen Peroxide

To an aqueous solution of 500 mg methylglucopyranoside and 250 mg manganese (II) nitrate, 10 ml 0.05 M bipyridyl solution and 50 mg TEMPO, 0.70 ml hydrogen peroxide (3% w/w) is added in portions of 20 μl in the course of 8 h. The pH of the mixture is kept between 6 and 7. The next day the mixture is treated with sodium chlorite to convert the aldehyde groups to carboxylic acid groups. (pH 4–5). The yield of uronic acid before and after further oxidation is 8 and 11%, respectively.

Example 3

C6 Oxidation of Methylglucopyranoside with TEMPO/Cu/Oxygen

Sixty mg of α-methylglucopyranoside, 500 mg TEMPO and 24 mg copper/histidine complex were dissolved in 100 ml of demineralised water. The reaction temperature was maintained at 30° C. and the pH was adjusted to 8.0. Oxygen was passed through the solution for two hours. After overnight reaction, the carboxyl content was determined using the Blumenkrantz method and found to be 17%.

Example 4

Oxidation of Pullulan by TEMPO/Mn/$H_2O_2$

In 50 ml of water 400 mg pullulan (2.4 mmol anhydroglucose units) and 50 mg of TEMPO were dissolved. To this solution 50 mg manganese nitrate and 5 ml bipyridine 0.05 M solution were added, followed by small amounts of hydrogen peroxide. (100 μl 3% w/v per time). The pH was maintained between 6.5 and 7.0. In total 2.0 ml hydrogen peroxide (3%) was added. After one day the aldehyde groups present were converted to carboxylic acid groups by reaction with sodium chlorite/hydrogen peroxide (pH 4–5). The yield of uronic acid with respect to groups was 25%.

Example 5

Oxidation of Pullulan by TEMPO/Mn/$H_2O_2$

In 25 ml of water 250 mg pullulan and 20 mg of TEMPO were dissolved. To this solution 25 mg manganese nitrate was added, followed by 100 μl of hydrogen peroxide (3% solution, w/w) and bipyridine solution (5 ml 0.05 M). The reaction was conducted at pH 6.5. At the first day 60 mg (1.8 mmol) hydrogen peroxide was added and after one day 25 mg of uronic acid was formed. During the second day 30 mg hydrogen peroxide was added and the amount of uronic acid was increased to 50 mg. The aldehyde groups were converted into carboxylic acid groups with hydrogen peroxide/sodium chlorite the content raised to 90 mg. (D.O. 60%). This example shows that higher levels of oxidising agent and longer reaction times lead to higher yields, compared to example 4.

Example 6

Oxidation of Pullulan with TEMPO/Mn/Oxygen

To a solution of 400 mg pullulan in 25 ml water 50 mg TEMPO, 180 mg manganese nitrate and 10 ml 0.05 M bipyridine were added. The pH was brought to 9 and oxygen gas was bubbled through the solution. A fast decrease in pH was observed. By addition of sodium hydroxide the pH of the solution was kept at 9. After one night of reaction the uronic acid content of the reaction mixture was determined according to the Blumenkrantz method 20% of uronic acid was formed.

Example 7

Oxidation of α-Methylglucopyranoside with Hydrogen Peroxide, Cobalt Chloride (II) and Bipyridine To a solution of 80 mg α-methylglucopyranoside and 25 mg TEMPO in 5 ml water, 2 ml of a 0.08M cobalt(II) chloride solution and 4 ml bipyridine solution were added. After adjusting the pH by addition of 0.05 M NaOH to 7, 50 ml hydrogen peroxide solution (3% w/w) was added. This resulted in a pH drop followed (usually after 10 to 15 minutes) by an increase When the pH was at its original value again, 50 ml hydrogen peroxide was added. In total 350 ml was added. After standing for one night the pH was brought to 3.5 and 100 ml hydrogen peroxide (30% w/w) and 100 mg sodium chlorite (Aldrich 80% purity) were added. After reacting for two hours the uronic acid content was determined. According to the Blumenkrantz method, before subsequent oxidation 9% and thereafter 12% uronic acid was formed.

Example 8

Oxidation of Pullulan with TEMPO/Co/Oxygen

A solution of 30 mmol cobalt (II) chloride, 60 mmol bipyridine, 450 mg pullulan and 25 mg TEMPO was exposed to oxygen in a closed system. A reaction to at least 20% conversion proceeds, as follows from the oxygen consumption (measured with a gas burette; the rate is 3 ml per hour).

What is claimed is:

1. A process for producing nitrosonium ions comprising oxidising a nitroxyl compound by subjecting the nitroxyl compound to the action of an oxidising agent in the presence of a complex of a transition metal and a complexing agent.

2. A process according to claim 1, wherein the nitroxyl compound is a di-tert-nitroxyl compound.

3. A process according to claim 1, wherein the transition metal is manganese, iron, cobalt, nickel, copper or vanadium.

4. A process according to claim 1, wherein the complexing agent is a nitrogen-containing compound.

5. A process according to claim 4, wherein the complexing agent is a bipyridyl or a triazonane or a (poly)histidine.

6. A process for oxidising a carbohydrate comprising producing nitrosonium ions by oxidising a nitroxyl compound with an oxidising agent in the presence of a complex of a transition metal and a complexing agent, and subjecting the carbohydrate to the action of an oxidising agent in the presence of said nitrosonium ions as a catalysts.

7. A process according to claim 6, wherein the carbohydrate is an α-glucan or fructan or a carboxymethylated, alkylated, or hydroxyalkylated derivative thereof.

8. A process according to claim 6, wherein the carbohydrate is hydroxyalkylated carbohydrate or a glycoside.

9. An oxidized carbohydrate, the carbohydrate being selected from disaccharides, oligosaccharides and polysaccharides of the α-glucan, mannan, galactan, fructan, and chitin types and carbohydrate glycosides, containing at least 1 cyclic monosaccharide group carrying a carbaldehyde group per 25 monosaccharide units and per molecule or a carboxymethylated, alkylated or hydroxyalkylated derivative thereof and further containing carboxyl and/or carboxymethyl groups.

10. An oxidised carbohydrate according to claim 9, containing at least 5 monosaccharide units per molecule.

11. An oxidized carbohydrate, the carbohydrate being selected from disaccharides, oligosaccharides and polysaccharides of the α-glucan, mannan, galactan, fructan, and chitin types and carbohydrate glycosides, containing at least 1 cyclic monosaccharide group carrying a carbaldehyde group per 25 monosaccharide units and per molecule or a derivative thereof in which derivative at least a portion of the carbaldehyde groups has been converted to a group with the formula —CH=N—R or —CH$_2$—NHR, wherein R is hydrogen, hydroxyl, amino, or a group $R^1$, $OR^1$ or $NHR^1$, in which $R^1$ is $C_1$–$C_{20}$ alkyl, $C_1$–$C_{20}$ acyl, a carbohydrate residue, or group coupled with or capable of coupling with a carbohydrate residue.

12. An oxidized carbohydrate, the carbohydrate being selected from disaccharides, oligosaccharides and polysaccharides of the α-glucan, mannan, galactan, fructan, and chitin types and carbohydrate glycosides, containing at least 1 cyclic monosaccharide group carrying a carbaldehyde group per 25 monosaccharide units and per molecule or a derivative thereof in which derivative at least a portion of the carbaldehyde groups has been converted to a group with the formula —CH($OR^3$)—O—CH$_2$—COOR$^2$ or —CH(—O—CH$_2$—COOR$^2$)$_2$, in which $R^2$ is hydrogen, a metal cation or an optionally substituted ammonium group, and $R^3$ is hydrogen or a direct bond to the oxygen atom of a dehydrogenated hydroxyl group of the carbohydrate.

13. A carbohydrate according to claim 11, further containing carboxyl and/or carboxymethyl groups.

14. A carbohydrate according to claim 12, further containing carboxyl and/or carboxymethyl groups.

* * * * *